United States Patent [19]

Adams et al.

[11] Patent Number: 5,736,529
[45] Date of Patent: Apr. 7, 1998

[54] USE OF NAD-RELATED COMPOUNDS IN THE TREATMENT OF NEURAL TRAUMA TO INHIBIT NEURODEGENERATION

[75] Inventors: James David Adams, La Crescenta; Lori Kathleen Klaidman, Santa Monica; Suman Kumar Mukherjee, Los Angeles, all of Calif.

[73] Assignee: Neurocal International Inc., Mountain View, Calif.

[21] Appl. No.: 624,291

[22] Filed: Mar. 22, 1996

[51] Int. Cl.⁶ .................................................. A61K 31/455
[52] U.S. Cl. ........................................ 514/46; 514/45
[58] Field of Search ......................... 536/26.24; 514/46, 514/44

[56] References Cited

U.S. PATENT DOCUMENTS 4,870,090  9/1989  Noda et al. .................. 514/355
5,594,011  1/1997  McDonald et al. ........... 514/343

FOREIGN PATENT DOCUMENTS 980721   12/1982  Russian Federation.
1152591  4/1985   Russian Federation.
1632428  3/1991   Russian Federation.

OTHER PUBLICATIONS

Beal, M. F., et al. 1994, Annals of Neurology vol. 36 No. 6 pp. 882–888, "Coenzyme $Q_{10}$ and Nicotinamide Block Striatal . . . ".
McBurney, in 'International Review of Neurobiology: Neuroprotective Agents and Cerebral Ischaemia', A. R. Green and A. J. Cross, eds., Academic Press, 1997, Chapter 8, pp. 173–195, especially pp. 174–175, 1997.
Adams, et al. (1989) "The acute histopathology of MPTP in the mouse" *Brain Res. Bull.* 23:1–17.
Adams et al. (1991) "Alzheimer's and Parkinson's disease. Brain levels of glutathione, glutathione disulfide and Vitamin E". *Mol. Chem. Neuropath.* 14:213–226.
Adams (1993) "New aspects of brain oxidative stress induced by tert-butylhydroperoxide" *Free Rad. Biol. Med.* 15:195–202.
Adams, et al. (1994) "The neuropathology of intracerebroventricular t-Butylhydroperoxide", *Molecular and Chemical Neuropathology*, 22:123–142.
Adams, et al. (1996) "Apoptosis and Oxidative Stress in the Aging Brain", *Annals. of N.Y. Acad. Sci.*, 786:135–151.
Adbel-Rahman, et al. "Protection of B cells against the effect of alloxan", *Toxlet* 02799:155–164.
Beal, (1994) "Neurochemistry and toxin models in Huntington's Disease", *Current Opinion in Neurology*, 7:542–547.
Beiswanger, et al. (1993) "3-acetylpyridine-induced degeneration in the dorsal root ganglia: involvement of small diameter neurons and influence of axotomy", *Neuropathology and Applied Neurobiology*, 19:164–172.
Berger N.A. (1985) "Poly(ADP-ribose)in the cellular response to DNA damage" *Rad. Res.* 101:4–15.

Berglund T. (1994) "Nicotinamide, a missing link in the early stress response in eukaryotic cells: a hypothesis with special reference to oxidative stress in plants" *FEBS Letters*, 351:145–149.
Boulikas T. (1991) "Relation between carcinogenesis, chromatin structure and poly (ADP-ribosylation)" *Anticancer Res.* 11:489–527.
Carson et al. (1986) "DNA strand breaks, NAD metabolism and programmed cell death" *Exp. Cell. Res.* 164:273–281.
Coppola, et al. (1995) "Different basal NAD levels determine opposite effects of poly(ADP-ribosyl) polymerase inhibitors on $H_2O_2$–induced apoptosis", *Experimental Cell Research*, 221:462–469.
de Ferreyra, et al. (1994) "Nicotinamide late protective effects against carbon tetrachloride–induced liver necrosis", *Experimental and Molecular Pathology*, 60:214–223.
Dettmers, et al. (1994) "Immersion and Perfusion staining with 2,3,5–triphenyltetrazolium chloride (TTC) compared to mitochondrial enzymes 6 hours after MCA–occlusion in primates", *Neurological Research* 16:205–208.
Eizirik, et al. (1994) "Nicotinamide decreases nitric oxide production and partially protects human pancreatic islets against the suppressive effects of combinations of cytokines", *Autoimmunity*, 19:193–198.
Gao, et al. (1994) "Activation of apoptosis in early mouse embryos by 2'-deoxyadenosine exposure", *Teratology*, 49:1–12.
Ghibelli, et al. (1995) "The increase in $H_2O_2$–induced apoptosis by ADP–ribosylation inhibitors is related to cell blebbing", *Experimental Cell Research*, 221:470–477.
Griffin, et al. (1995) "The role of inhibitors of poly(ADP–ribose) polymerase as resistance–modifying agents in cancer therapy", *Biochimie*, 77:408–422.
Hauschildt, et al. (1992) "Induction of nitric oxide synthase in L929 cells by tumour–necrosis factor α is prevented by inhibitors of poly(ADP-ribose) polymerase", *Biochem J.*, 288:255–260.

(List continued on next page.)

*Primary Examiner*—David Guzo
*Assistant Examiner*—Matthew Latimer
*Attorney, Agent, or Firm*—Burns, Doane, Swecker & Mathis, L.L.P.

[57] ABSTRACT

The present invention is directed to methods for reducing the degree of neural degeneration in a mammal due to acute neural trauma by the administration of a NAD-related compound and for kits useful in the method. NAD-related compounds include quinolinic acid; quinolinic acid ribonucleotide; nicotinamide; nicotinic acid; nicotinic acid ribonucleotide; nicotinic acid ribonucleotide, reduced form; nicotinamide ribonucleotide; nicotinamide ribonucleotide, reduced form; nicotinic acid adenine dinucleotide; nicotinic acid adenine dinucleotide, reduced form; nicotinamide adenine dinucleotide (NAD); nicotinamide adenine dinucleotide phosphate (NADP); nicotinamide adenine dinucleotide, reduced form (NADH); and nicotinamide adenine dinucleotide phosphate, reduced form (NADPH) and pharmaceutically acceptable salts thereof.

10 Claims, 5 Drawing Sheets

OTHER PUBLICATIONS

Hayaishi O. and Ueda K. (1977) "Poly (ADP–ribose) and ADP–ribosylation of proteins", *Annu. Rev. Biochem.* 46:95–116.

Hoshino, et al. (1993) "3–Aminobenzamide protects the mouse thymocytes in vitro from dexamethasone–mediated apoptotic cell death and cytolysis without changing DNA strand breakage", *J. Steroid Biochem. Molec. Biol.*, 44(2):113–119.

Kawabata, et al. (1992) "Effects of nicotinamide and its isomers on iron–induced renal damage", *Acta Pathologica Japonica*, 42(7):469–475.

Keller, et al. (1971) "Studies on the biosynthesis of NAD from nicotinamide and on the intracellular pyridine nucleotide cycle in isolated perfused rat liver", *Eur J Biochem* 22:263–270.

Khachaturian Z.S. (1985) "Diagnosis of Alzheimer's disease" *Arch. Neurol.* 42:1097–1105.

Klaidman, et al. (1995) "High–performance liquid chromatography analysis of oxidized and reduced pyridine dinucleotides in specific brain regions", *Analytical Biochemistry*, 228:312–317.

Kuroda, et al. (1996) "Secondary bioenergetic failure after transient focal ischaemia is due to mitochondrial injury", *Acta Physiol Scand* 156:149–150.

LeDoux, et al. (1988) "Mechanisms of nicotinamide and thymidine protection from alloxan and streptozocin toxicity", *Diabetes*, 37:1015–1019.

Linnik et al. (1993) "Evidence supporting a role for programmed cell death in focal cerebral ischemia in rats" *Stroke* 24:2002–2009.

Martin, et al. (1994) "Biochemical modulation of tumor cell energy in vivo: II. A lower dose of adriamycin is required and a greater antitumor activity is induced when cellular energy is depressed", *Cancer Investigation*, 12(3):296–307.

McKhann et al. (1984) "Clinical diagnosis of Alzheimer's disease: Report of the NINCDS–ADRDA work group under the auspices of the Department of Health and Human Services task force of Alzheimer's disease", *Neurology* 34:939–944.

Monti, et al. (1992) "Apoptosis–programmed cell death: a role in the aging process?", *Am. J. Clin. Nutr,* 55:1208S–1214S.

Monti, et al. (1994) "Cell death protection by 3–aminobenzamide and other poly(ADP–ribose) polymerase inhibitors: different effects on human natural killer and lymphokine activated killer cell activities", *Biochemical and Biophysical Research Communications*, 199(2):525–530.

Morimoto and Bonavida (1992) "Diphtheria toxin– and Pseudomonas A toxin–mediated apoptosis", *The Journal of Immunology*, 149(6):2089–2094.

Mukherjee, et al. (1995) "Apoptosis and DNA fragmentation as induced by t–Butylhydroperoxide in the brain", *Annual Meeting Oxygen Club of California*, p. 109.

Mukherjee, et al. (1995) "Apoptosis and DNA fragmentation as induced by tertiary butylhydroperoxide in the brain", *Brain Res. Bull.*, 38(6):595–604.

Munson (1985) "Pharmacology of nutrients and nutritional diseases", *Principals of pharmacology: basic concepts and clinical applications*, Chapman and Hall, pp. 954–958.

Nicholson et al. (1995) "Identification and inhibition of the ICE/CED–3 protease necessary for mammalian apoptosis", *Nature*, 376:37–43.

Nosseri et al. (1994) "Possible involvement of poly (ADP–ribosyl) polymerase in triggering stress–induced apoptosis" *Exp. Cell Res.* 212:367–373.

Odunze et al. (1990) "MPTP toxicity in the mouse brain and vitamin E" *Neurosci. Lett.* 108:346–349.

Popick (1975) "Application of a new intraventricular injection technique in rat brain norepinephrine studies" *Life Sci* 18:197–203.

Rabinovitch, et al. (1994) "DNA fragmentation is an early event in cytokine–induced islet beta–cell destruction", *Diabetologia*, 37:733–738.

Ray, et al. (1992) "$Ca^{++}$–activated DNA fragmentation and dimethylnitrosamine–induced hepatic necrosis: Effects of $Ca^{++}$–endonuclease and poly(ADP–Ribose) polymerase inhibitors in mice", *The Journal of Pharmacology and Experimental Therapeutics*, 263(1):387–394.

Satoh et al. (1993) "$NAD^+$–dependent repair of damaged DNA by human cell extracts" *J. Biol. Chem.* 268(8):5480–5487.

Schraufstatter, et al. (1986) "Hydrogen peroxide–induced injury of cells and its prevention by inhibitors of poly(ADP–ribose) polymerase", *Proc. Natl. Acad. Sci. USA*, 83:4908–4912.

Slonim, et al. (1976) "Effect of streptozotocin on red–blood––cell–reduced glutathione: modification by glucose, nicotinamide, and epinephrine", *Diabetes*, 25(3):216–222.

Steller (1995) "Mechanisms and genes of cellular suicide" *Science* 267:1445–1449.

Stryer, Lubert (1975) "Chapter 25: Biosynthesis of nucleotides", *Biochemistry* p. 617.

Suarez–Pinzon, et al. (1994) "Mechanisms of cytokine–induced destruction of rat insulinoma cells: the role of nitric oxide", *Endocrinology* 134(3):1006–1010.

Sugimura et al. (1992) "Regulation of DNA polymerase β by poly (ADP–ribose) polymerase" in *ADP–ribosylation Reactions* (Poirier G.G. and Moreau P., eds), pp. 276–281. Springer–Verlag, New York.

Thomas, et al. (1995) "Tumour oxygenation, radiosensitivity, and necrosis before and/or after nicotinamide, carbogen and perflubron emulsion administration", *Int. J. Radiat. Biol.*, 67(5):597–605.

Tominaga et al. (1993) "Endonuclease activation following focal ischemic injury in the rat brain" *Brain Res.* 608:21–26.

Wakade, et al. (1995) "Deoxynucleoside induces neuronal apoptosis independent of neurotrophic factors", *The Journal of Biological Chemistry*, 270(30):17986–17992.

Watson, et al. (1995) "Poly(Adenosine Diphosphate Ribose) polymerase inhibition prevents necrosis induced by $H_2O_2$ but not apoptosis", *Gastroenterology*, 109:472–482.

Weller, et al. (1992) "Niacinamide blocks 3–acetylpyridine toxicity of cerebellar granule cells in vitro" *Brain Research*, 594:160–164.

Wilson, et al. "Mechanisms of streptozotocin– and alloxan–induced damage in rat B cells", *Diabetologia*, 587–591.

Yamada, et al. (1993) "Effects of free radical scavengers on cytokine actions on islet cells", *Acta Endocrinologica*, 128:379–384.

Yoshida S. and Simbulan C.M.G. (1994) "Interaction of poly (ADP–ribose) polymerase with DNA polymerase α." *Mol. Cell Biochem.* 138:39–44.

Poster abstract–1995.

USE OF NAD-RELATED COMPOUNDS IN THE TREATMENT OF NEURAL TRAUMA TO INHIBIT NEURODEGENERATION

BACKGROUND OF THE INVENTION

1. Field of the Invention

The present invention is directed to methods for reducing the degree of neural degeneration in a mammal due to acute neural trauma by the administration of a NAD-related compound.

The methods of this invention are directed to the discovery that neural degeneration due to necrosis and apoptosis in mammals exposed to acute neural trauma can be reduced by the administration of a NAD-related compound.

2. References

The following publications and patent application are cited in this application as superscript numbers at the relevant portion of the application:

1. Adams (1993) "New aspects of brain oxidative stress induced by tert-butylhydroperoxide" *Free Rad. Biol. Med.* 15:195–202
2. Popick, (1975) "Application of a new intracerebroventricular injection technique in rat brain norepinephrine studies" *Life Sci* 18:197–204
3. Odunze et al. (1990) "MPTP toxicity in the mouse brain and vitamin E" *Neurosci. Lett.* 108:346–349
4. Berger N. A. (1985) "Poly(ADP-ribose) in the cellular response to DNA damage" *Rad. Res.* 101:4–15
5. Adams et al. (1994) "The neuropathology of intracerebroventricular t-butlyhydroperoxide" *Mol. Chem. Neuropath.* 22:123–142
6. Steller (1995) "Mechanisms and genes of cellular suicide" *Science* 267:1445–1449
7. Linnik et al. (1993) "Evidence supporting a role for programmed cell death in focal cerebral ischemia in rats" *Stroke* 24:2002–2009
8. Nosseri et al. (1994) "Possible involvement of poly (ADP ribosyl) polymerase in triggering stress-induced apoptosis" *Exp. Cell Res.* 212, 367–373.
9. Hayashi O. and Odeka K. (1977) Poly (ADP-ribose) and ADP-ribosylation of proteins. *Annu. Rev. Biochem.* 46, 95–116.
10. Berglund T. (1994) "Nicotinamide, a missing link in the early stress response in eukaryotic cells: a hypothesis with special reference to oxidative stress in plants" *FEBS Letters*, 351, 145–149.
11. Carson et al. (1986) "DNA strand break, NAD metabolism and programmed cell death" *Exp. Cell. Res.* 164, 273–281.
12. Boulikas T. (1991) "Relation between carcinogenesis, chromatin structure and poly (ADP-ribosylation)" *Anticancer Res.* 11, 489–528.
13. Yoshida S. and Simbulan C. M. G. (1994) "Interaction of the poly (ADP-ribose) polymerase with DNA polymerase α." *Mol. Cell Biol.* 138, 39–44.
14. Sugimura et al. (1992) "Regulation of DNA polymerase β by poly (ADP-ribose) polymerase in ADP-ribosylation reactions" (Poirier G. G. and Moreau O., eds), pp. 276–281. Springer-Verlag, N.Y.
15. Saroh et al. (1993) "NAD$^+$-dependent repair of damaged DNA by human cell extracts". *J. Biol. Chem.* 268(8), 5480–5487.
16. Nicholson et al. (1995) "Identification and inhibition of the ICE/CED-3 protease necessary for mammalian apoptosis". *Nature.* 376, 37–43.
17. Mukherjee et al. (1995) "Apoptosis and DNA fragmentation as induced by tertiary butylhydroperoxide in the brain". *Brain Res. Bull.* 38(6), 595–604.
18. McKhann et al. (1984) "Clinical diagnosis of Alzheimer's disease: Report of the NINCDS-ADRDA work group under the auspices of the Department of Health and Human Services task force of Alzheimer's disease". *Neurology.* 34, 939–944.
19. Tominaga et al. (1993) "Endonuclease activation following focal ischemic injury in the rat brain". *Brain Res.* 608, 21–26.
20. Khachaturian Z. S. (1985) "Diagnosis of Alzheimer's disease". *Arch. Neurol.* 42, 1097–1105.
21. Adams et al. (1991) "Alzheimer's and Parkinson's disease. Brain levels of glutathione, glutathione disulfide and Vitamin E".*Mol. Chem. Neuropath.* 14, 213–226.
22. Adams, et al. (1989) "The acute histopathology of MPTP in the mouse" *Brain Res. Bull.* 23, 1–17.
23. Klaidman, et al. (1995) "High performance liquid chromatography analysis of oxidized and reduced pyridine dinucleotides in specific brain regions". *Anal. Biochem.* 228, 312–317.

All of the above publications and patent applications are herein incorporated by reference in their entirety to the same extent as if each individual publication or patent application was specifically and individually indicated to be incorporated by reference in its entirety.

3. Description of the Related Art

Reactive oxygen species have been implicated in neurodegenerative disorders involving diseases that do not involve specific neurons in the brain such as stroke, ruptured berry aneurysm and physical trauma to the head. The cell loss that is associated with such disorders may be due to necrosis or apoptosis. The death of neurons is particularly important because neurons do not replicate in mature mammals.

Cell death can occur by either apoptosis or necrosis. Cell death by necrosis occurs due to severe injurious changes in the cell environment. Necrotic death is characterized by a generalized breakdown of cellular structure and function followed by cell lysis and tissue inflammation. Necrosis can occur almost immediately on administration of sufficiently high doses of toxin or other insults.

Apoptosis, on the other hand, is a slower process. Multicellular organisms appear to have an inherent ability to control cell death by activating an internally encoded suicide program that induces apoptosis[6]. It appears to be an active process of cellular self-destruction involving a series of cellular events that require active cell participation (e.g. macromolecular synthesis and enzyme activation). Apoptotic death is characterized by cell shrinkage, membrane blebbing and fragmentation of nuclear DNA into oligonucleosome subunits. Nuclear DNA is fragmented into nucleosome-sized pieces of approximately 200 bp[7] and multiples thereof, generating 3' OH groups at the strand breaks. Ultimately the nucleus fragments into small condensed, membrane bound apoptotic bodies. The process of apoptosis is usually asynchronous within a cell population. In vivo, apoptotic cells can be cleared rapidly by phagocytosis.

Apoptosis could be a way of self-elimination of potentially mutant cells that have experienced sublethal DNA damage. There may be a cellular mechanism which can quantify the damage to DNA and translate it into a message of cell suicide. A likely candidate for this may be the chromatin bound enzyme poly(ADP-ribose) polymerase (PADPRP)[8]. PADPRP is known to activate some DNA repair enzymes and inhibit the activity of other DNA repair enzymes. This enzyme cleaves NAD+ to yield nicotinamide and ADP ribose. The same enzyme polymerizes successive ADP ribose residues to synthesize poly(ADP-ribose)[9]. NAD is thus degraded to nicotinamide[10]. PADPRP is activated by various types of stress that cause strand breakage in DNA like oxidative stress, radiation and mutagens. It has been observed that under conditions of severe stress, this enzyme, in trying to repair damaged DNA can use up almost all of the intracellular NAD, thus inducing ATP depletion and cell death[11].

Several biochemical alterations have been proposed as the basis for the irreversible injury that may follow exposure of cells to activated oxygen species. The activated oxygen radical species generated during oxidative stress may cause lipid peroxidation, oxidation of protein thiols and DNA damage.

The brain is the organ most vulnerable to oxidative stress due to its high consumption of oxygen and lack of regenerative ability. In the cell, DNA may be vulnerable to damage. Proteins and lipid membranes can be replaced if the damage is not too extensive. However, DNA may be irreparably damaged in some oxidative insults due to fragmentation, double stand breaks and base modifications such as thymine dimers, which may be difficult to repair. This could cause the cells to permanently malfunction.

There is a need to identify methods to prevent necrosis and apoptosis of neurons upon exposure to acute neural trauma. This invention is directed to the discovery that apoptosis and possibly necrosis can be reduced if NAD-related compounds are administered to a mammal either before or shortly after exposure of the mammal to acute trauma.

Further advantages of the present invention will become apparent from the following description of the invention with reference to the attached drawings.

SUMMARY OF THE INVENTION

The present invention is directed to a method for reducing the degree of neural degeneration in a mammal due to an acute neural trauma which method comprises administering to the mammal an effective amount of a pharmaceutical composition comprising an NAD-related compound.

The present invention is also directed to a method for reducing the degree of neural degeneration in a mammal due to exposure to an acute neural trauma which method comprises administering to the mammal a pharmaceutical composition comprising from about 1 to about 600 mg/kg of an NAD-related compound.

The present invention is also directed to a kit for reducing the degree of neural degeneration in a mammal exposed to an acute neural trauma comprising an NAD-related compound and a container.

DESCRIPTION OF THE PREFERRED EMBODIMENTS

As noted above, the present invention relates to methods for reducing the degree of neural degeneration in a mammal due to exposure to an acute neural trauma by the administration of an NAD-related compound.

However, prior to discussing this invention in further detail, the following terms will first be defined.

1. Definitions

As used herein the following terms have the definitions given below:

Acute neural trauma includes those traumas that do not affect only specific neurons. Thus acute neural trauma includes, by way of example, stroke, ruptured berry aneurysm, physical trauma, such as a blow to the head and epilepsy.

The term "mammal" includes humans.

The term "NAD-related compounds" includes, quinolinic acid; quinolinic acid ribonucleotide; nicotinamide; nicotinic acid; nicotinic acid ribonucleotide; nicotinic acid ribonucleotide, reduced form; nicotinamide ribonucleotide; nicotinamide ribonucleotide, reduced form; nicotinic acid adenine dinucleotide; nicotinic acid adenine dinucleotide, reduced form; nicotinamide adenine dinucleotide (NAD); nicotinamide adenine dinucleotide phosphate (NADP); nicotinamide adenine dinucleotide, reduced form (NADH); and nicotinamide adenine dinucleotide phosphate, reduced form (NADPH) and pharmaceutically acceptable salts thereof. All of these chemicals are commercially available or are generally known. Preferably the NAD-related compound is nicotinamide or nicotinic acid, more preferably the NAD-related compound is nicotinamide. In any event, the NAD-related compounds other than NAD, NADH, NADPH OR NADP, must be capable of entering the enzymatic pathways available in the mammalian body resulting in the production of NAD or NADH.

The term "pharmaceutically acceptable salts" includes the pharmaceutically acceptable addition salts of NAD-related compounds and are derived from a variety of organic and inorganic counter salts well known in the art and include, by way of example only, sodium, potassium, calcium magnesium, ammonium, tetralkylammonium and the like.

3. Methodology

As shown below in the examples, NAD-related compounds are effective in reducing the degree of neural degeneration induced by acute neural trauma to the brain in a mammal.

Examples 1–8 demonstrate that if the NAD-related compound is administered to a mammal after an acute neural trauma, the degree of neural degeneration observed in the mammal is reduced.

In view of the above, it is contemplated that a pharmaceutical composition comprising the NAD-related compound could be administered in a prophylactic manner. If the neural traumatic event is anticipated, the NAD-related compounds are preferably administered to the mammalian patient on a daily basis such that preferably the NAD-related compound is administered between about 14 hours before the event and the event, more preferably between about 10 hours before the event and the event, and most preferably between about 4 hours before the event and the event. It is contemplated that the administration of the NAD-related compounds could be continued after the event, most preferably up to about 3 weeks after the event, more preferably up to about 2 weeks after the event and most preferably up to about 72 hours after the event.

If the acute neural trauma was not anticipated, a pharmaceutical composition comprising the NAD-related compounds could be administered up to about 3 weeks after the traumatic event, more preferably, up to about 2 weeks after the traumatic event and still more preferably up to about 72 hours after the traumatic event.

The pharmaceutical composition comprising the NAD-related compounds may be administered in a single dose, in multiple doses or in a continuous perfusion over the critical time period.

NAD-related compounds are effective in reducing the neural degeneration in a traumatized mammal when administered at a dosage range of from about 1 mg to about 600 mg/kg of body weight, and preferably from about 20 to about 100 mg/kg of body weight. The specific dose employed is regulated by the particular type of trauma being treated as well as by the judgement of the attending clinician depending upon factors such as the severity of the trauma, the age and general condition of the patient, and the like. The pharmaceutical compositions described herein can be administered in a single dose or in multiple doses or in a continuous infusion over the critical time frame.

The pharmaceutical compositions comprising the NAD-related compounds are preferably administered parenterally, intranasally, intrapulmonarily, transdermally, intravenously and intra-arterially, although other forms of administration are contemplated. The pharamceutical composition comprising the NAD-related compound can be formulated into such dosage forms as tablets, granules, powders, capsules, suspensions, injections, suppositories etc. by a routine method in the field of formulation technology.

The methods of this invention are preferably achieved by use of a pharmaceutical composition suitable for use in the parenteral administration of an effective amount of the NAD-related compound. This composition comprises a pharmaceutically inert carrier such as water, buffered saline etc. and an effective amount of an NAD-related compound so as to provide the above-noted dosage of the NAD-related compound when administered to a patient. It is contemplated that suitable pharmaceutical compositions can additionally contain optional components such as a preservative, etc.

It is further contemplated that other suitable pharmaceutical compositions can include oral compositions, transdermal compositions or bandages, biodegradable slow-release polymers etc., which are well known in the art.

It is still further contemplated that the NAD-related compound can be incorporated as a part of a liposome or a micelle which can then be formulated into a pharmaceutical composition.

As can be appreciated from the disclosure above, the present invention has a wide variety of applications.

Accordingly, the following examples are offered by way of illustration and not by way of limitation.

EXAMPLES

In the examples below, the following abbreviations have the following meanings. If not defined below, then the abbreviations have their art recognized meanings.

NAD—nicotinamide adenine dinucleotide
NADH—nicotinamide adenine dinucleotide, reduced form
NADP—nicotinamide adenine dinucleotide phosphate
NADPH—nicotinamide adenine dinucleotide phosphate, reduced form
tBuOOH—t-butylhydroperoxide
mg—milligram
kg—kilogram
μl—microliter
μM—micromolar
ip—intraperitonially
ICV—intracereboventricular
EDTA—ethylenediamine tetraacetic acid
HPLC—high performance liquid chromatography
PBS—phosphate buffered saline
DMPO—5,5'-dimethyl-1-pyrroline-N-oxide
EPR—electronic paramagnetic resonance
HO.—hydroxyl radical
DETAPAC—diethylene triamine pentacetic acid
MPTP—1-methyl-4-phenyl-1,2,3,6-tetrahydropyridine In general male C57BL/6 mice (2, 8 or 24 months old) were anesthetized with ketamine and xylazine (200 and 2 mg/kg, ip). They were injected ICV with tBuOOH in doses of approximately 22 or 110 mg/kg. This amounts to 1 or 5 μl of a 70% solution of tBuOOH injected slowly into a lateral cerebral ventricle. A mouse brain weighs about 400 mg. The doses of tBuOOH amount to about 0.25–1.25% of the brain weight. Animals recovered from anesthesia about 30 minutes or so after tBuOOH administration. The high dose mice frequently appeared inactive until death at about 2 hours after treatment. The low dose animals move about freely and resemble mice treated ICV with 0.9% saline. Low dose mice survived for 48 hours or more.

tBuOOH is a lipophillic organic hydroperoxide that is detoxified by glutathione peroxidase. Unlike hydrogen peroxide, it is not a substrate for catalase. It is a relatively stable compound which can readily permeate throughout the brain and can inflict damage on all types of brain cells, like neurons, astrocytes, pericytes, oligodendrocytes and endothelial cells[5].

Example 1

HPLC Determination of tBuOOH in Mice Brains

Male C57BL/6 mice, 8 months old, were treated ICV with 110 mg/kg of tBuOOH. At various times, brains were removed, dissected and frozen on dry ice. Later the brains were homogenized in acetonitrile and centrifuged for 5 minutes at 12,000 g. The supernatants were injected onto a reverse phase HPLC column (Biophase ODS, 5μ, Bioanalytical Systems, West Lafayette, Id.) as previously described by Adams et al.[1] The mobile phase was 67% (30 mM ammonium sulfate, 1 mM EDTA (pH 6.5)) and 33% acetonitrile at a flow rate of 1 ml/min. tBuOOH was detected by electrochemical detection at −0.3 V.

Figure 1:
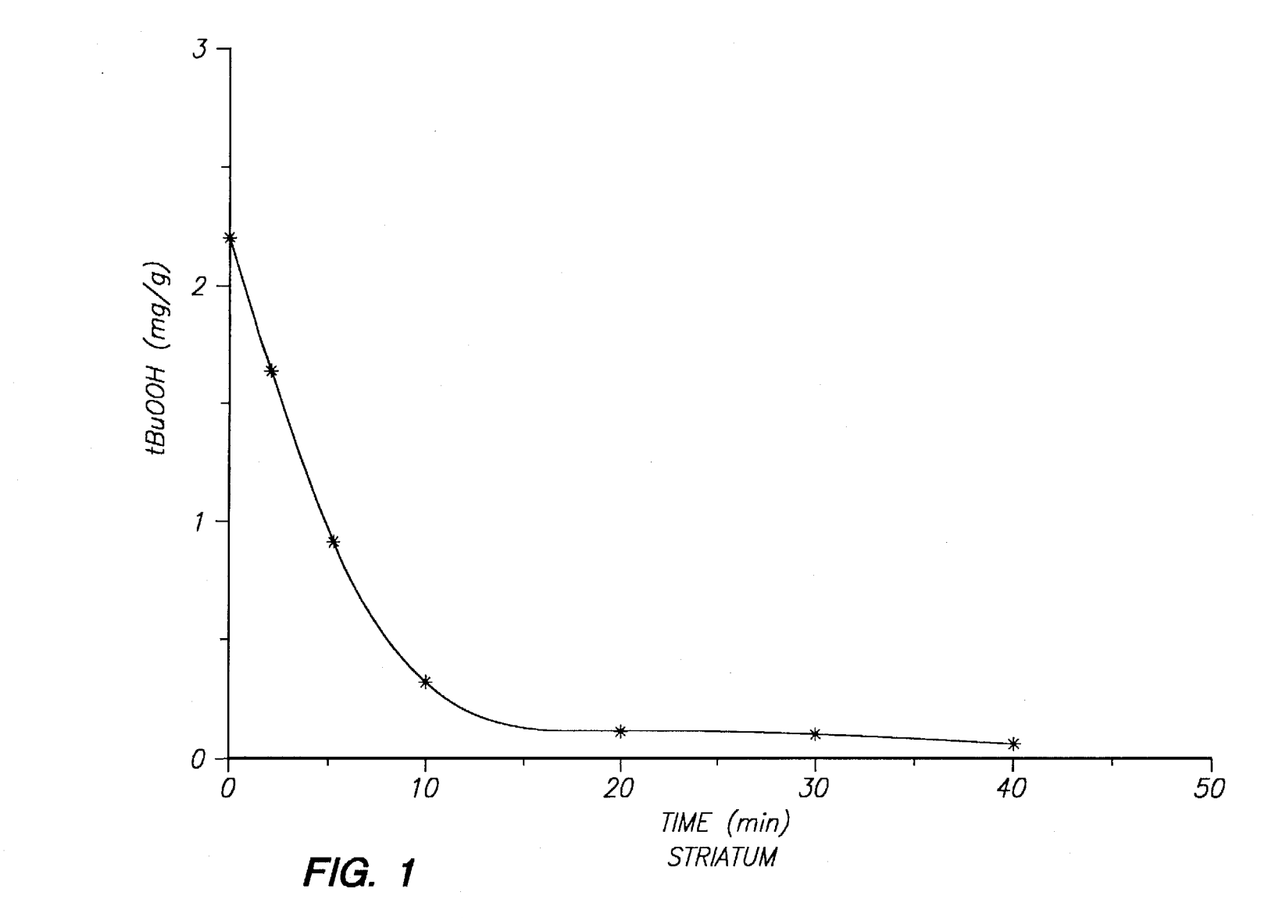
FIG. 1 illustrates the pharmacokinetic profile in the striatum of mice treated with tBuOOH.

FIG. 1 shows the tBuOOH pharmacokinetic profile in the striatum of 8 month old mice. The data show a very rapid clearance of tBuOOH from the brain in the initial period, followed by a slower clearance. Following ICV administration of even large doses (110 mg/kg) of tBuOOH, the toxin concentrations drop within 5 minutes to less than 50% of the initial concentration. By 10 minutes the concentration of tBuOOH in the brain is about 1 mM. This is quickly eliminated with a half-life of 4–20 minutes, depending on the brain region. A virtually identical curve was generated with 2 month old mice.

Therefore, it is expected that with low doses of tBuOOH (22 mg/kg), the tBuOOH concentrations in the brain will be about 200 μM at 10 minutes after administration and decrease quickly from there.

Example 2

DNA Fragmentation upon treatment with tBuOOH

Young adult (2 month old) and mature (8 month old) C57BL/6 mice were divided into 7 groups with 8 animals in the control group and 4 animals in each of the other groups for both the age groups. A dose of 109.7 mg/kg of tBuOOH was administered ICV, to three groups of mice of both age groups. See Tables 1 and 2. tBuOOH was injected ICV following the technique described in Popick[2]. The experiments ended 2 minutes, 5 minutes and 20 minutes after injection of tBuOOH. In the second set of experiments, 21.9 mg/kg of the toxin was administered ICV in the other three groups of mice with experimental durations of 12 hours, 24 hours and 48 hours respectively. The controls were treated with saline rather than tBuOOH.

The brains were removed after the allotted time period and sectioned immediately into the following sections: cortex, striatum, hippocampus, thalamus, midbrain and cerebellum. A volume of 0.2 ml of ice cold lysing buffer (10 mM Tris-HCl, pH 7.5, 1 mM EDTA, and 0.2% Triton X-100) was added to each section which was centrifuged at 12,000 g for 25 minutes to separate the intact from the fragmented DNA. The supernatant (containing the fragmented DNA) was transferred to a separate tube. 0.2 ml of the lysing buffer was added to the pellet with sonication for 10 seconds. The amount of DNA in the supernatant and pellet fractions was determined by a fluorimetric method, using the dye Hoechst 33258 (Sigma Chemical Co., St. Louis Mo.). DNA damage is presented as the ratio of DNA in the supernatant to the total DNA in the pellet and supernatant per gram of tissue.

TABLE 1

Fraction of damaged DNA in 8 month old C57BL/6 mice

| Amount tBuOOH | Time after tBuOOH | Cortex | Hippo | Striatum | Thalamus | Midbrain | Cerebellum |
|---|---|---|---|---|---|---|---|
| Control |  | 0.56 ± 0.14 | 0.46 ± 0.06 | 1.25 ± 0.60 | 1.05 ± 0.41 | 1.39 ± 0.63 | 0.53 ± 0.13 |
| 109.7 mg | 2 min. | 0.87 ± 0.17 | 0.69 ± 0.14 | 1.56 ± 0.27 | 2.29 ± 0.78* | 2.24 ± 0.66 | 0.80 ± 0.09 |
| 109.7 mg | 5 min. | 0.67 ± 0.16 | 0.81 ± 0.20*[1] | 1.63 ± 0.47 | 1.86 ± 0.58 | 1.93 ± 0.26 | 1.15 ± 0.12* |
| 109.7 mg | 20 min. | 0.70 ± 0.19 | 0.67 ± 0.15 | 2.38 ± 0.41* | 2.77 ± 0.30* | 2.98 ± 0.85* | 1.46 ± 0.36* |
| 21.9 mg | 12 hours | 0.61 ± 0.10 | 0.46 ± 0.17 | 1.17 ± 0.33 | 1.08 ± 0.30 | 0.76 ± 0.24 | 0.69 ± 0.15 |
| 21.9 mg | 24 hours | 0.65 ± 0.13 | 0.46 ± 0.05 | 0.99 ± 0.06 | 0.75 ± 0.27 | 1.05 ± 0.35 | 0.67 ± 0.16 |
| 21.9 mg | 48 hours | 0.69 ± 0.10 | 0.55 ± 0.06 | 1.15 ± 0.12 | 1.65 ± 0.13 | 1.05 ± 0.13 | 1.01 ± 0.11* |

Results have been given as mean ±SD and can be expressed as fraction of DNA damaged per gram of tissue.
*Statistically significantly different from corresponding control values by ANOVA and Newman-Keul's test ($p < 0.05$)
[1]Statistically significantly different from corresponding values in the other age group by Student's t-test ($p < 0.05$)

TABLE 2

Fraction of damaged DNA in 2 month old C57BL/6 mice

| Amount tBuOOH | Time after tBuOOH | Cortex | Hippo | Striatum | Thalamus | Midbrain | Cerebellum |
|---|---|---|---|---|---|---|---|
| Control |  | 0.66 ± 0.22 | 0.38 ± 0.05 | 1.35 ± 0.51 | 1.54 ± 0.66 | 1.30 ± 0.76 | 0.67 ± 0.28 |
| 109.7 mg | 2 min. | 0.84 ± 0.33 | 0.66 ± 0.09* | 2.00 ± 0.45 | 2.66 ± 0.33* | 2.48 ± 1.02* | 1.17 ± 0.25 |
| 109.7 mg | 5 min. | 0.82 ± 0.23 | 0.41 ± 0.05 | 1.66 ± 0.52 | 2.85 ± 0.83* | 1.71 ± 0.77 | 0.88 ± 0.20 |
| 109.7 mg | 20 min. | 0.76 ± 0.26 | 0.66 ± 0.14* | 2.56 ± 0.49* | 2.46 ± 0.65 | 3.09 ± 0.28* | 1.39 ± 0.51* |
| 21.9 mg | 12 hours | 0.53 ± 0.16 | 0.40 ± 0.16 | 1.13 ± 0.49 | 1.29 ± 0.39 | 0.83 ± 0.58 | 0.65 ± 0.19 |
| 21.9 mg | 24 hours | 0.47 ± 0.13 | 0.31 ± 0.04 | 1.16 ± 0.31 | 1.44 ± 0.76 | 1.23 ± 0.12 | 0.93 ± 0.36 |
| 21.9 mg | 48 hours | 0.73 ± 0.03 | 0.50 ± 0.09 | 1.66 ± 0.33 | 1.25 ± 0.14 | 1.24 ± 0.13 | 1.29 ± 0.12*[1] |

Results have been given as mean ±SD and can be expressed as fraction of DNA damaged per gram of tissue.
*Statistically significantly different from corresponding control values by ANOVA and Newman-Keul's test ($p < 0.05$)
[1]Statistically significantly different from corresponding values in the other age group by Student's t-test ($p < 0.05$)

In both the 2 month and 8 month old mice, the cortex was not affected by either the high dose or the low dose of tBuOOH over a prolonged period of time. All other sections in the brain, for both age groups, showed some vulnerability either to the high dose or the low dose or both.

In the hippocampus, in the case of the 8 month old mice, significant damage was seen within 5 minutes of administration of 109.7 mg/kg of tBuOOH. In the case of the 2 month old age group, however, significant damage was seen 2 minutes and 20 minutes after injection. The damage seen at 5 minutes after injection in the 2 month old mice was significantly lower than that visualized in the case of the other age group. Thus it seems that the hippocampus of the older mouse may be more vulnerable to attack by reactive oxygen species. This may be one of the reasons why the 8 month old mouse brain is more prone to injury by free radical generating compounds.

In the striatum, for both age groups, significant DNA damage was found only after 20 minutes of treatment with the high dose of the toxin. In the thalamus, significant DNA damage was found after 2 minutes of treatment in both the age groups. While significant damage was seen again after 20 minutes in the 8 month old mice, it was seen again after 5 minutes of treatment in the 2 month old mice.

In the midbrain, significant damage was found after 20 minutes of treatment in both the groups. Significant damage was observed after 5 minutes and 20 minutes, in the case of the 8 month old cerebellum and after 20 minutes in the 2 month old cerebellum. Moreover significant damage was observed in the cerebellum at the end of 48 hours for both the age groups, though, the damage found in the case of the 2 month old age group was significantly greater than that for the 8 month old mice.

Figure 2:
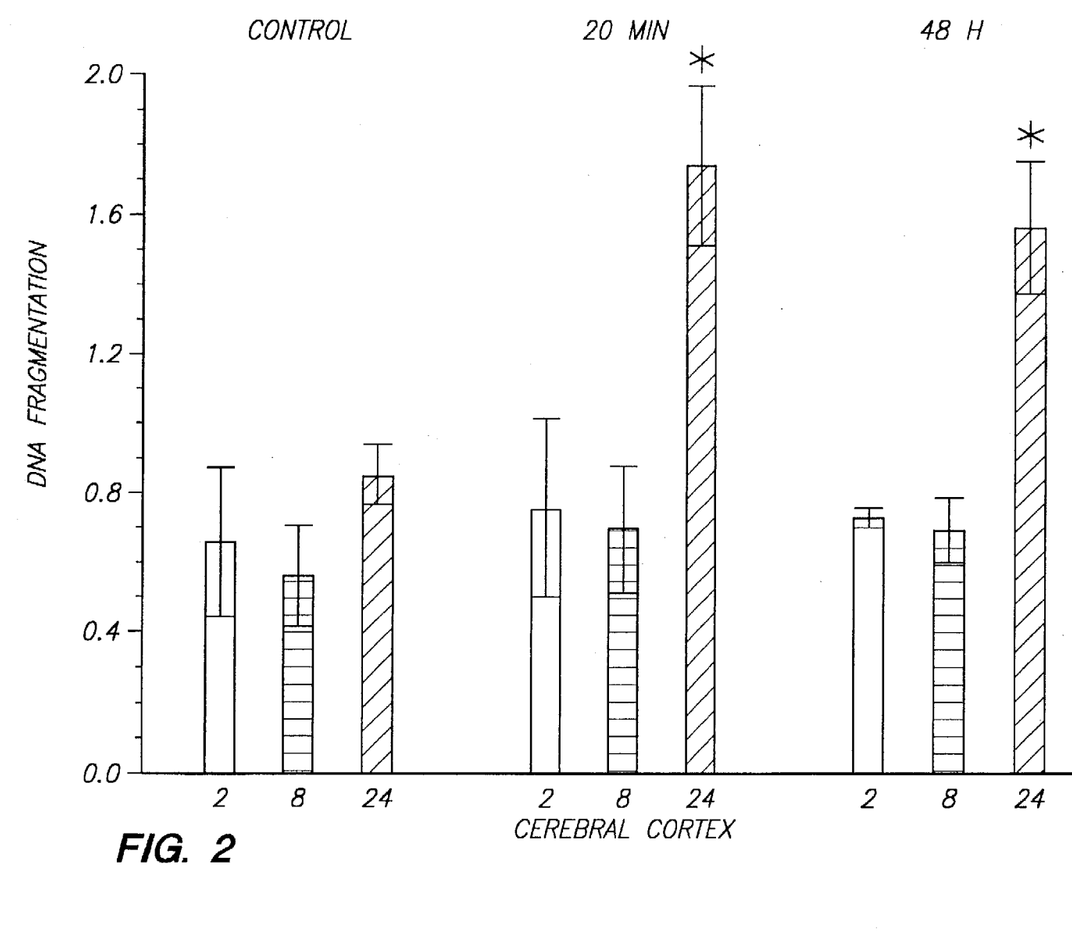
FIG. 2 illustrates the DNA fragmentation in the cerebral cortex of mice treated with tBuOOH. *Significantly different from 24 month old control values by ANOVA and Newman-Keul's test.

A second experiment was conducted to measure the degree of DNA fragmentation. FIG. 2 shows the effect of tBuOOH induced DNA fragmentation in the cerebral cortex. Male C57BL/6 mice, of ages 2, 8 or 24 months old, were treated with tBuOOH ICV. Mice in the 20 minute group were treated with 110 mg/kg of tBuOOH and maintained for 20 minutes until brains were removed and analyzed for DNA fragmentation. This dose of tBuOOH induces cellular necrosis in a number of brain regions. Mice in the 48 hour group were given 22 mg/kg of tBuOOH and maintained for 48 hours. This dose of tBuOOH induces apoptosis and a small amount of necrosis in a number of brain regions.

It was found that DNA fragments appear in the brain within 2 minutes of the tBuOOH administration. DNA fragmentation is a very early event in tBuOOH toxicity, as is glutathione oxidation.

In 2 and 8 month old mice, there is no increase in DNA fragmentation in the cortex. However, 24 month old mice show a robust increase in DNA fragmentation in the cortex. This may imply that 24 month old mice have impaired DNA protective mechanisms or DNA repair mechanisms, as compared to younger mice. Alternatively, tBuOOH may produce more radicals in the nuclei of 24 month old mice than in younger animals. The pattern of DNA fragmentation in the cerebral cortex of 24 month old mice after tBuOOH administration was also found in the hippocampus. The increase in DNA fragments in 24 month old mice at 20 minutes after 110 mg/kg of tBuOOH demonstrates that DNA fragmentation is involved in the induction of necrosis in brain cells. In younger mice, the cerebral cortex is resistant to this mechanism of induction of necrosis.

It was also found that mixing DNA and tBuOOH produces HO. and other radicals, which can be detected by EPR in the presence of DMPO[23]. Therefore, DNA fragmentation is produced following HO. and other radicals induced DNA damage. Necrotic degeneration probably occurs within the first few hours after tBuOOH administration.

Apoptosis is probably involved in DNA fragmentation detected at 48 hours after 22 mg/kg of tBuOOH (FIG. 2). Apoptosis involves activation of endonuclease which cleaves damaged DNA into fragments. By 48 hours after tBuOOH administration, the induction of necrosis will have subsided, such that DNA fragmentation associated with necrosis will no longer be apparent. Apoptosis is a delayed event which occurs in cells damaged enough to impair their survival, but not damaged enough to induce necrosis.

Figure 3:
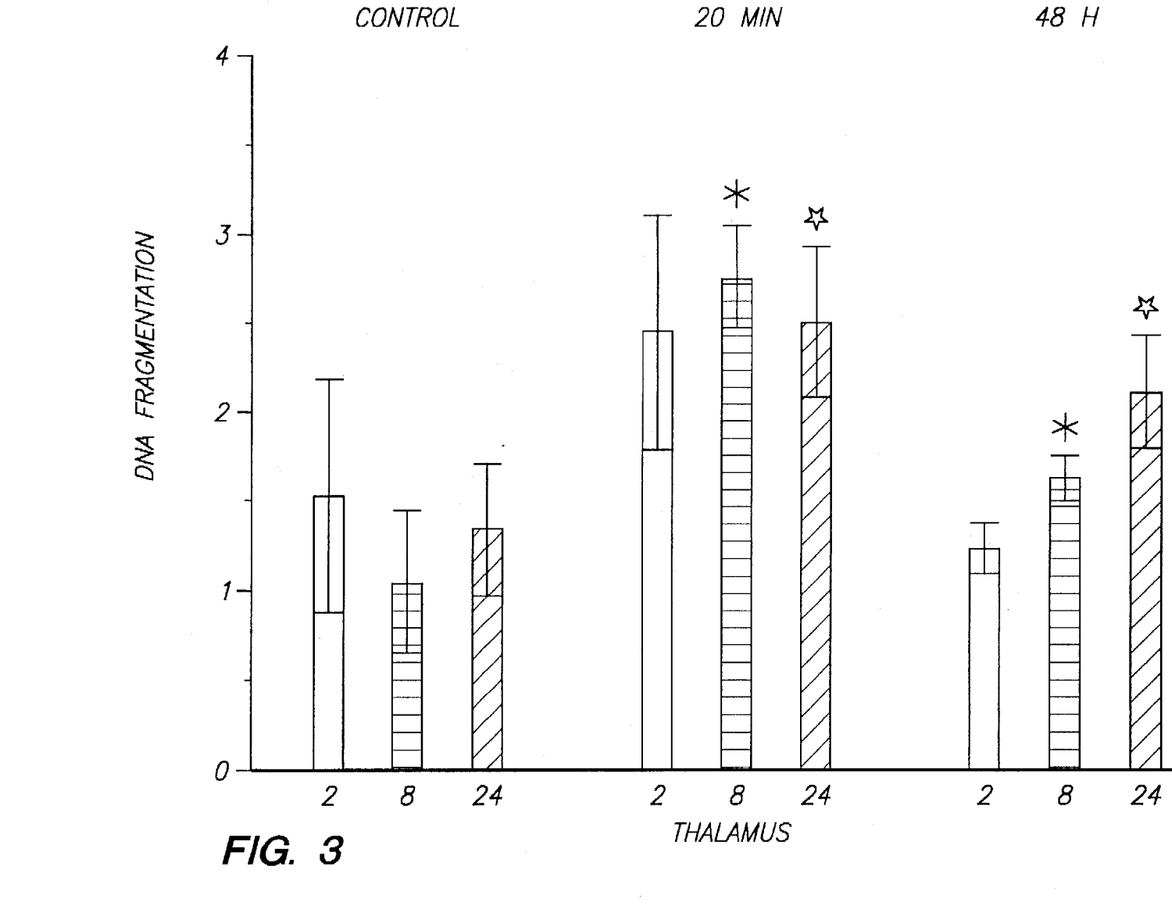
FIG. 3 illustrates the DNA fragmentation in the thalamus of mice treated with tBuOOH. *Significantly different from 8 month old control values by ANOVA with Newman-Keul's test. Star—Significantly different from 24 month old control values by ANOVA with Newman-Keul's test.

DNA fragmentation is important in the thalamus following tBuOOH administration. See FIG. 3. This figure shows that 8 and 24 month old mice are more sensitive than 2 month old mice to tBuOOH induced necrosis in the thalamus at 20 minutes. The tBuOOH induced necrosis in the thalamus involved DNA fragmentation. The DNA fragmentation in the thalamus is representative of DNA fragmentation in the striatum, cerebellum and midbrain. Mice, 2 months old, also demonstrated increased DNA fragmentation, the probable cause of necrosis, in the striatum, midbrain and hippocampus after treatment with tBuOOH.

Apoptosis induced DNA fragmentation was found only in 24 month old mice in the thalamus, 48 hours after tBuOOH administration. The results shown in FIGS. 1 and 2 demonstrate that 24 month old mice are more susceptible to apoptosis than are younger mice. This increased susceptibility of 24 month old mice was found in every brain region except the cerebellum. In the cerebellum, DNA fragmentation increased significantly in 2, 8 and 24 month old mice at 48 hours after administration. Therefore, it appears that the cerebellum is the brain region most susceptible to apoptosis.

Example 3

Effect of Administration of Nicotinamide before Toxin

Figure 4:
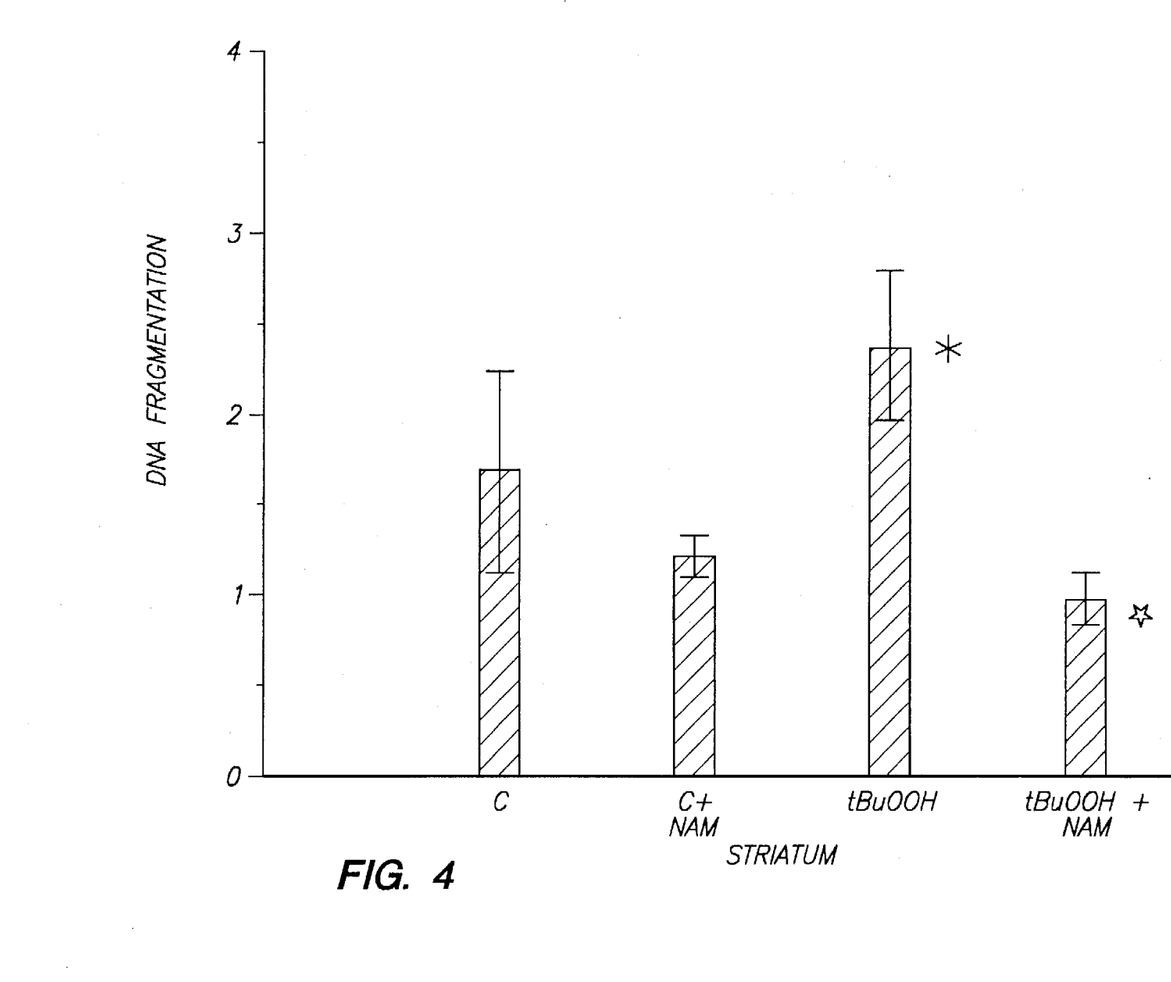
FIG. 4 illustrates the DNA fragmentation in the striatum of mice pretreated with nicotinamide and then treated with tBuOOH. * Significantly different from control values by ANOVA with Newman-Keul's test. Star—Significantly different from tBuOOH data by ANOVA with Newman-Keul's test.

Nicotinamide (500 mg/kg, ip) was administered to male C57BL/6 mice, 8 months old. 13 hours later the mice were injected ICV with tBuOOH (110 mg/kg) and maintained for 20 minutes. The brains were removed and analyzed for DNA fragmentation. FIG. 4 shows that nicotinamide prevents the DNA fragmentation that produces necrosis. Control mouse results are labeled "C". Therefore, nicotinamide can protect cells from DNA fragmentation associated necrosis and apoptosis.

Example 4

Pyridine Dinucleotide Quantitation

Male C57 B 1/6 mice, 8 months old, were treated ICV with tBuOOH (110 mg/kg) and maintained for 2, 5, 20 or 120 minutes. Anesthetized tBuOOH treated mice were immersed in liquid nitrogen to freeze their brains. The frozen brains were removed and dissected over dry ice. The brain regions were homogenized and analyzed by HPLC to determine NAD, NADH, NADP and NADPH levels as described previously. It is very important to stabilize the pyridine dinucleotides to prevent artifactual oxidation. NAD and NADP were stabilized by homogenization of brain regions in a cyanide containing solution. The cyanide reacts with the compounds forming cyano adducts that are stable. NADPH and NADH were stabilized by homogenizing brain regions in basic solution. NADPH and NADH are stable in base. Fortunately, the cyanide reaction proceeds optimally in base. Therefore, use of basic cyanide solutions during the homogenization produced optimal stabilization of NAD, NADP, NADH and NADPH. Following extraction with chloroform, centrifugation at 12,000 g for 5 minutes at 5° C., and filtration through 0.45μ positively charged nylon filters to remove DNA, the supernatants were injected onto a reverse phase HPLC column ("REXCHROME" ODS 5μ, Regis, Morton Grove, Ill.). Fluorescence detection (330 nm, excitation, 460 nm emission) was used to detect fluorescent NADH, NADPH and the cyano adducts of NAD and NADP.

NADPH is oxidized rapidly following tBuOOH administration to 8 month old mice but recovers just as rapidly. This rapid oxidation of NADPH following tBuOOH administration was found in every brain region. NADPH levels increase to control values within 5 minutes after tBuOOH administration. This does not parallel glutathione oxidation, where glutathione disulfide levels continue to be elevated at 5 minutes and later after tBuOOH administration to 8 month old mice[1]. This may be due to an apparent loss of glutathione disulfide reductase activity during tBuOOH induced toxicity in 8 month old mice[3].

NAD is slowly and partially depleted following tBuOOH administration to 8 month old mice. NAD levels decline in many brain regions following tBuOOH administration. NAD is a cosubstrate for poly(ADP-ribose) polymerase, which is activated during the apoptosis process. Poly(ADP-ribose) polymerase transfers ADP-ribose moieties from NAD to various substrates, which activates DNA ligase and inactivates $Ca^{+2}$, $Mg^{+2}$ endoglucanase, thus stimulating DNA repair[4]. However, NAD and ATP can become depleted during this process, which might produce inadequate poly (ADP-ribose) polymerase activity. Inadequate poly(ADP-ribose) polymerase activity might allow accumulation of DNA damage perhaps leading to apoptosis.

Nicotinamide was administered to some mice (500 mg/kg) 13 hours before tBuOOH administration. Nicotinamide inhibits poly(ADP-ribose) polymerase.[3] However, nicotinamide levels at 13 hours after administration, i.e. at the time of administration of the tBuOOH, should have dropped to control levels. Therefore the nicotinamide should not have inhibited the poly(ADP-ribose) polymerase upon tBuOOH administration.

Nicotinamide is a precursor for NAD. The results showed that nicotinamide produced about a 130% increase in brain levels of NAD at 8 to 13 hours after administration of the nicotinamide. This increase in NAD levels may protect cells from the depletion of NAD during the activation of poly (ADP-ribose) polymerase.

Example 5

Apoptosis Visualization

The purpose of the apoptosis staining was to identify individual cells that may have undergone apoptosis. Residues of digoxigenin nucleotide were added to the DNA by an enzyme terminal deoxynucleotidyl transferase (TdT) which catalyzes the addition of deoxyribonucleotide triphosphate to the 3'-OH end of single and double stranded DNA. Thus the targets for labeling are the numerous new 3'-OH DNA ends generated by DNA fragmentation, easily observable in morphologically identifiable nuclei and apoptotic bodies. The sections were then incubated with an antibody to digoxigenin residues. The antibody was coupled to peroxidase allowing visualization with 3,3'-diaminobenzidine. Other sections were stained with cresyl violet. The rationale for selecting this method was that the single cell sensitivity of this method is far higher than that of a standard agarose gel or other histochemical staining method.

The cresyl violet staining was done to examine whether the damage observed after administration of the low dose of tBuOOH was solely due to apoptosis or whether it was a mixture of apoptosis and necrosis.

A dose of 21.9 mg/kg of tBuOOH was administered ICV to C57BL/6 mice. The mice were anesthetized 48 hours after the tBuOOH administration and perfused through the left cardiac ventricle with 0.175M sodium phosphate and 0.155M sodium chloride (pH 7.5, PBS), then with 4% formaldehyde and 0.2% glutaraldehyde in PBS for six minutes with each solution at room temperature. The brains were then removed from the cranium after 2 hours of fixation and sliced coronally into 50μ sections with a vibrating microtome.

In order to detect individual cells undergoing apoptosis, the In Situ Apoptosis Detection Kit, (Oncor, Gaithersburg, Md.) was used. In brief the tissues were quenched in 2% hydrogen peroxide ($H_2O_2$) in PBS to deactivate endogenous peroxidase and then two drops of equilibration buffer containing potassium cacodylate were applied. After incubation for 10–15 seconds, 54 μl of working strength terminal deoxynucleotidyl transferase (TdT) enzyme was pipetted onto each section and incubated for 1 hour in a humidified chamber. The tissues after incubation were washed in a prewarmed working strength stop/wash buffer and incubated further for 30 minutes. Then 2 drops of anti-digoxigenin-peroxidase was then added to the sections. The tissues were again incubated for 30 minutes at room temperature. $H_2O_2$ was added to a filtered solution of freshly prepared 3,3'-diaminobenzidine tetrahydrochloride-2-hydrate (DAB) and used to stain sections at room temperature. The tissues were put on slides, air dried, washed in three changes of xylene and mounted with balsam.

For electron microscopy, the sections were treated with 2% osmium tetroxide, dehydrated, mounted in eponaraldite, thin sectioned, mounted on grids and stained with uranyl acetate and lead citrate[5]. The mice used for electron microscopy were treated with 109.7 mg/kg tBuOOH ICV.

For cresyl violet staining, the sections were mounted on gel coated slides. The slides were immersed for 5 minutes in each of the following: xylene, xylene, 100% alcohol, 100%, 95% and 70% alcohol. They were dipped in distilled water and stained in 0.5% cresyl violet for 5 minutes. They were differentiated in water for 3–5 minutes and dehydrated through 70%, 95% 100% and 100% alcohol. They were then put in xylene and cover-slipped with balsam.

Apoptotic cells were discovered in the brains of tBuOOH treated mice. Apoptotic cells were found in many brain regions, but were most abundant in the thalamus and pons. Cells undergoing apoptosis are characterized by immunohistochemical staining of DNA fragments in the nuclei and cytoplasm. Vacuoles are typically present in the condensed cytoplasm. DNA fragments are not usually visualized in the neurites. Apoptotic bodies can frequently be seen in the areas where apoptotic cells are seen. Apoptotic bodies are the remnants of ruptured, condensed apoptotic cells, and are rich in DNA fragments. Some of the sections stained for apoptotic cells demonstrate faintly stained cells that are of essentially normal size. These cells may be in the very early stages of apoptosis, such that small amounts of DNA fragments are present in the nucleus and cytoplasm. These normal sized cells demonstrate that all of the darkly stained cells are very shrunken.

Cresyl violet staining demonstrated that apoptotic cells frequently have condensed nuclei and cytoplasms. The nucleic may be fragmented in the cells. The cytoplasms are usually dark and vacuolated.

Necrotic cells frequently have swollen cytoplasms which may contain vacuoles. Nuclei of necrotic cells are usually pyknotic, but are not fragmented. Apoptotic cells are easily distinguished from necrotic cells, by the condensed cytoplasms and fragmenting nuclei. The necrotic cells observed did not demonstrate DNA fragment staining. Apparently, waiting 48 hours for the development of apoptosis, precludes the detection of DNA fragments in necrotic cells. Alternatively necrotic cells may not contain high enough levels of DNA fragments to allow immunohistochemical visualization.

Nicotinamide administration completely prevented apoptosis 48 hours following 22 mg/kg of tBuOOH. 500 mg/kg of nicotinamide was administered intraperitoneally 13 hours before the administration of tBuOOH and the mice treated as described above. The sections from nicotinamide pretreated tBuOOH treated mice, stained for DNA fragments are identical to control sections. There are no apoptotic bodies or cells containing DNA fragments in any of the sections. This matches well with the DNA fragmentation data in that nicotinamide completely prevents tBuOOH induced DNA fragmentation. Cresyl violet staining of nicotinamide pretreated, tBuOOH treated mice demonstrate that the vast majority of neurons appear normal. Some neurons have somewhat condensed cytoplasms, but normal nuclei. The condensed cytoplasms do not contain vacuoles. These cells are clearly not apoptotic, but may have some of the cytoplasmic changes associated with early phases of the apoptotic process. Therefore, nicotinamide appears to inhibit DNA damage associated with tBuOOH administration. This may protect brain cells from necrosis or apoptosis.

Example 6

Effect of the Administration of Nicotinamide with Toxin 24 month old C57BL/6 mice were divided into 3 groups of 3 mice each. One group was the control. A second group of mice was treated ICV with 109.7 mg/kg t-BuOOH and then sacrificed 20 minutes later. A third group of mice were treated ICV with 21.9 mg/kg t-BuOOH and then sacrificed 48 hours later. The fourth group of mice were treated ICV with 21.9 mg/kg t-BuOOH and 500 mg/kg nicotinamide simultaneously and then sacrificed 48 hours later. The brains were removed from the treated mice and were sectioned into the following six regions: cortex, striatum, hippocampus, thalamus, midbrain and cerebellum. DNA damage has been expressed as a ratio of the damaged DNA to the total DNA per gram of tissue.

DNA fragmentation was assessed in 50 μg samples of tissue from a brain region. A volume of 0.2 ml of ice cold lysing buffer (10 mM Tris-HCl, pH 7.5, 1 mM EDTA, and 0.2% Triton X-100) was added to each section, which was then centrifuged at 12,000 g for 25 minutes to separate the intact from the fragmented DNA. The supernatant (containing the fragmented DNA) was transferred to a separate tube. 0.2 ml of the lysing buffer was added to the pellet with sonication for 10 seconds. The amount of DNA in the supernatant and pellet fractions was determined by a fluorimetric method, using the dye Hoechst 33258. DNA damage is presented as the ratio of DNA in the supernatant to the total DNA in the pellet and supernatant per gram of tissue[17].

8 month old mice were divided into 4 groups (n=5 each). Group 1 was the control. Mice in group 2 were treated with 109.7 mg/kg t-BuOOH and then sacrificed 20 minutes later. Mice in group 3 was injected simultaneously with 109.7 mg/kg t-BuOOH and 500 mg/kg nicotinamide and then sacrificed 20 minutes later. Mice in group 4 were treated simultaneously with 21.9 mg/kg t-BuOOH and 500 mg/kg nicotinamide and then sacrificed 48 hours later. The same procedures were performed as with the 24 month old mice.

TABLE 3

DNA FRAGMENTATION IN 24 MONTH OLD MICE

|  | cortex | striatum | hippo | thala | midbrain | cerebellum |
| --- | --- | --- | --- | --- | --- | --- |
| control | 0.86 ± 0.09 | 1.03 ± 0.22 | 0.71 ± 0.38 | 1.35 ± 0.38 | 1.36 ± 0.21 | 0.99 ± 0.22 |
| 109.7 mg/kg t-BuOOh. 20 min. | 1.73 ± 0.23* | 2.46 ± 0.33* | 1.44 ± 0.20* | 2.52 ± 0.43* | 2.77 ± 0.65* | 1.84 ± 0.45* |
| 21.9 mg/kg t-BuOOH. 48 hours | 1.55 ± 0.19* | 1.94 ± 0.31 | 1.43 ± 0.23* | 2.13 ± 0.31* | 2.04 ± 0.53* | 1.71 ± 0.45* |
| 21.9 mg/kg t-BuOOh + 500 mg/kg nic. 48 hours | 1.05 ± 0.24 | 1.30 ± 0.22 | 0.75 ± 0.08 | 1.22 ± 0.23 | 1.43 ± 0.24 | 1.10 ± 0.30 |

*Statistically significantly different from the corresponding control values by ANOVA and Newman-Keul's test (p < 0.05).

TABLE 4

DNA FRAGMENTATION IN 8 MONTH OLD MICE TREATED WITH tBUOOH ALONE OR WITH tBUOOH + NICOTINAMIDE

|  | cortex | striatum | hippo | thala | midbrain | cerebellum |
| --- | --- | --- | --- | --- | --- | --- |
| control | 0.61 ± 0.14 | 1.07 ± 0.18 | 0.56 ± 0.15 | 1.05 ± 0.22 | 1.05 ± 0.31 | 0.68 ± 0.13 |
| 109.7 mg/kg t-BuOOH | 0.83 ± 0.14 | 2.33 ± 0.46* | 0.768 ± 0.16 | 2.65 ± 0.88* | 2.37 ± 0.43* | 1.16 ± 0.15* |

TABLE 4-continued

DNA FRAGMENTATION IN 8 MONTH OLD MICE TREATED WITH tBUOOH ALONE OR WITH tBUOOH + NICOTINAMIDE

| | cortex | striatum | hippo | thala | midbrain | cerebellum |
|---|---|---|---|---|---|---|
| 109.7 mg/kg t-BuOOH + 500 mg/kg nic. 20 min. | 0.76 ± 0.15 | 2.48 ± 0.55* | 0.74 ± 0.14 | 2.50 ± 0.63* | 2.46 ± 0.81* | 1.29 ± 0.31* |
| 21.9 mg/kg t-BuOOH + 500 mg/kg nic. 48 hours | 0.56 ± 0.06 | 1.12 ± 0.24 | 0.57 ± 0.11 | 1.09 ± 0.27 | 1.12 ± 0.17 | 0.84 ± 0.11 |

*Statistically significantly different from the corresponding control values by ANOVA and Newman-Keul's test ($p < 0.05$).

A gel electrophoresis was performed to investigate whether the DNA fragmentation that is observed at the end of 48 hours is due to apoptosis or not (FIG. 7). 8 month old C47BL/6 mice were treated with ICV with 21.9 mg/kg t-BuOOH 48 hours prior to removal of the brains. Brains were added to lysing buffer and centrifuged. The supernatants were collected as in the DNA fragmentation assay. The samples were extracted with an equal volume of phenol/chloroform/isoamyl alcohol (25:24:1). The DNA in the aqueous phase was precipitated by adding an equal volume of 100% ethanol and maintained at −20° C. overnight. DNA was collected by centrifugation at 12,000 g for 25 minutes, air dried and resuspended in TBE buffer (90 mM Tris, 90 mM boric acid and 2 mM EDTA, pH 8.0). Horizontal electrophoresis was performed for 2 hours at 100 volts in a 0.75% agarose gel with TBE buffer. The gel was stained with ethidium bromide and photographed by UV transillumination. Oligosomal sized DNA fragments were observed along with a smear of fragmentation from late-stage necrosis.

Significant DNA fragmentation was observed in many brain regions after administration of 109.7 mg/kg t-BuOOH in both 24 month and 8 month old C57BL/6 mice (Tables 3 and 4 respectively). In the 8 month old mice, however, there was no significant increase in DNA fragmentation in the cortex or hippocampus, when compared to the corresponding controls. The 24 month old mouse experienced extensive DNA damage in almost every brain region at every dose of tBuOOH. This implies that 24 month old mice are more susceptible to damage to DNA than are the younger mice.

The difference in vulnerability to DNA damage was more apparent when 21.9 mg/kg t-BuOOH was administered to both the age groups of the mice (Tables 3 and 4). In the case of the 8 month old mice, significantly higher DNA fragmentation values were seen only in the cerebellum (FIG. 7). On the other hand, significant increases in DNA fragmentation were observed in almost all brain regions (except the striatum), in case of the 24 month old mice. This indicates that the older mice are more prone to suffer from DNA damage when compared to younger mice.

In the gel electrophoresis experiment two distinct patterns of DNA degradation, the 'smear' as well as the 'ladder' formations could be observed. Without being limited, it is thought that calcium dependent proteinases may be activated, which digest the histone proteins leading to the destruction of the nucleosomal structure. If the stimulation of proteinases occur prior to the activation of the endonucleases, degradation of histones allows random access of endonucleases to host DNA. This results in non-specific DNA cleavage, which in turn results in a 'smear' on gel electrophoresis. If, on the other hand, the activation of $Ca^{2+}$—$Mg^{2+}$—dependent endonucleases precede that of proteinases, DNA cleavage can occur at internucleosomal linker regions with conservation of the nucleosomal core structure, producing a nucleosome-sized 'ladder' pattern. This 'ladder' pattern is a characteristic feature of apoptosis[19].

It appears that the induction of necrosis or apoptosis is a dose dependent phenomenon[17]. The dose of t-BuOOH that was used for the gel electrophoresis experiment may have been sufficient for some neurons to undertake the necrotic pathway of cell death. For some other types of neurons, the dose may have been sufficient to induce apoptosis and not necrosis. Other neurons may have the capability to protect themselves against the levels of t-BuOOH that were introduced. This may explain why both the 'smear' and the 'ladder' patterns of DNA degradation were observed in our study.

When nicotinamide was administered along with t-BuOOH to mice of both age groups, it was found that nicotinamide was not able to prevent the DNA fragmentation observed 20 minutes after the high dose of t-BuOOH. An important point to be noted in this regard is that nicotinamide was also not found to increase DNA fragmentation when administered simultaneously with t-BuOOH. The fact that nicotinamide may be able to cause an increase in DNA fragmentation has been suggested in some studies, due to the inhibitory effect that it exerts on PADPRP[12].

Figure 5:
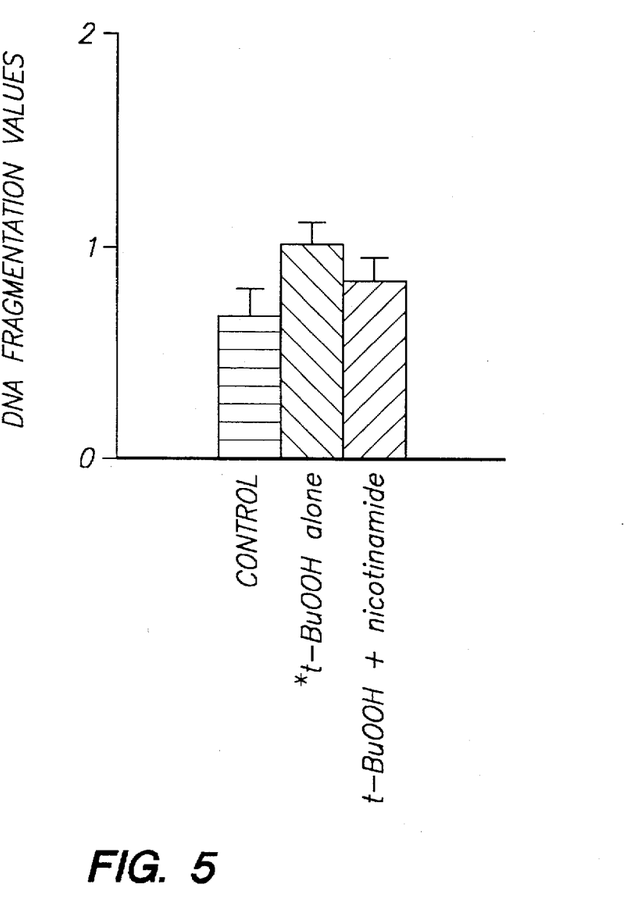
FIG. 5 illustrates the extent of DNA fragmentation in the cerebellums of 8 month old mice treated with tBuOOH in the presence or absence of nicotinamide. *Statistically significantly different from control values and tBuOOH with nicotinamide by ANOVA with Newman-Keul's test. ($p<0.05$)

However, when nicotinamide was injected simultaneously with 21.9 mg/kg t-BuOOH, DNA fragmentation was found to decrease 48 hours later in almost all brain regions in the 24 month old mice (Table 3). The DNA fragmentation at that time point can be associated with both apoptosis as well as late-stage necrosis. Three out of six 24 month old mice died when only 21.9 mg/kg t-BuOOH was injected. On the other hand one out of six mice died when 500 mg/kg nicotinamide was administered simultaneously with the neurotoxin. Nicotinamide also prevented DNA fragmentation in the cerebellums of 8 month old mice treated with 21.9 mg/kg of t-BuOOH (FIG. 5). Nicotinamide, which is a precursor of NAD in the brain, may thus be able to prevent DNA fragmentation induced by active oxygen species. Clearly nicotinamide has no effect on DNA fragmentation that is induced by necrosis 20 minutes following a high dose of t-BuOOH. This may be due to two reasons: [1] nicotinamide injected ip, may not be available at the end of 20 minutes in the brain, even though it is the most effective precursor of NAD in the brain; and [2] nicotinamide, acting by itself as an inhibitor of PADPRP, may not be able to prevent the fragmentation of DNA. Nicotinamide was able to prevent DNA fragmentation when it was administered 13 hours prior to t-BuOOH injection in a previous study. However, by that time all the nicotinamide may have been converted to NAD, as seen from the elevated levels of the pyridine nucleotide following administration of nicotinamide.

The exact role of PADPRP at the site of DNA strand breaks is not clear. In some studies in vitro, it has been reported that PADPRP helps in DNA repair by inhibiting replication and by helping to locate the repair enzymes, such as ligases, at the site of DNA fragmentation[13]. In one study, however, it was observed that PADPRP provides sterical hindrance to the entry of enzymes like DNA polymerase β at the site of the DNA strand breaks, and thus inhibits (or at least slows down) the process of DNA repair[14]. This observation is supported by the fact that PADPRP exists in 10-fold excess compared to other enzymes and is present in excess of the levels that are required for poly-(ADP-ribose) synthesis[15]. In a number of studies, PADPRP has been shown to be catalytically cleaved by a cysteine proteinase, apopain, before the onset of apoptosis[16]. However, this proteolytic cleavage probably affects only some of the PADPRP enzymes, leaving some active.

Therefore, DNA is a primary target of radical attack in the brain, as a widespread and consistent level of DNA damage within 20 minutes of administration of a radical-generating neurotoxin was observed. The susceptibility to DNA damage is related to the age of the animals, as older animals were found to be more prone to DNA fragmentation. Nicotinamide was found to prevent DNA fragmentation, most probably by preventing the loss of NAD, which is induced by the stimulation of PADPRP due to DNA strand breaks.

Example 7

Analysis of human brain tissue

AD and PD are both neurodegenerative diseases associated with age. Active oxygen radicals have also been implicated in the induction of both of these disorders.

Human brain tissues were obtained from the Alzheimer's Disease Research Center Consortium at the University of Southern California and the Division of Neurological Surgery, University of California, Irvine. Diagnosis of Alzheimer's disease (AD) was done in patients, based on the NINCDS-ADRDA criteria[18]. Neuropathological confirmation of AD was performed according to the modification of a diagnostic protocol[20], as established by the Consortium to Establish a Registry in Alzheimer's disease (CERAD). This protocol is based on neocortical plaque scores which are age-related and then combined with a clinical history of dementia. Parkinson's disease (PD) was confirmed on detection of Lewy bodies in catecholaminergic neurons and on nerve cell loss in the zona compacta of the substantia nigra. In all cases, the presence of PD or AD was defined by histopathological evaluation of brain material. Patients grouped as AD-PD either developed dementia after PD or were first diagnosed with AD and later developed PD[21].

Brains from 13 patients with AD, 7 with AD-PD and 4 with no neurological disease were dissected at autopsy and cut into 3 cm blocks from specific brain regions. These regions were frontal cortex (Brodman's area 9), hippocampus, putamen, caudate nucleus, midbrain and medulla. The postmortem time was purposefully kept to a minimum and the tissues were frozen at −100° C. till the time of the experiment.

DNA fragmentation was assessed in 50 μg samples of tissue from a brain region. A volume of 0.2 ml of ice cold lysing buffer (10 mM Tris-HCl, pH 7.5, 1 mM EDTA, and 0.2% Triton X-100) was added to each section, which was then centrifuged at 12,000 g for 25 minutes to separate the intact from the fragmented DNA. The supernatant (containing the fragmented DNA) was transferred to a separate tube. 0.2 ml of the lysing buffer was added to the pellet with sonication for 10 seconds. The amount of DNA in the supernatant and pellet fractions was determined by a fluorimetric method, using the dye Hoechst 33258. DNA damage is presented as the ratio of DNA in the supernatant to the total DNA in the pellet and supernatant per gram of tissue.

Patients with AD-PD differed clinically from those with AD alone, as the patients with AD alone were found to survive longer (about 1 year) after diagnosis, than the patients with AD-PD. Significant increases in DNA fragmentation were observed in some human brain regions from patients who had suffered from AD or AD-PD, when compared to agematched controls (Table 6). In the case of AD patients a significantly higher DNA fragmentation value was found in the hippocampus and in the putamen. However an increase in DNA fragmentation in the A9 region was not observed. Damage to the A9 region has been implicated in AD. This may be due to a limitation in the method used or it may be because of the fact that DNA fragments are removed very efficiently by DNA repair enzymes. For the AD-PD patients, a significantly higher level of DNA fragmentation was observed in the mesencephalon. This region contains the dopaminergic neurons that are particularly affected in PD.

TABLE 5

CHARACTERISTICS OF PATIENTS

| | AGE (years) | ILLNESS DURATION (years) | POST MORTEM TIME (hours) |
| --- | --- | --- | --- |
| Control | 78 ± 16.62 | 0 | 7.08 ± 2.80 |
| AD | 79.46 ± 7.98 | 1–9 | 4.30 ± 3.36 |
| AD-PD | 78.14 ± 7.20 | 1–7 AD 0–14 PD | 3.71 ± 2.12 |

Postmortem time is the time from death until brain samples were frozen at −70° C.

TABLE 6

DNA FRAGMENTATION IN AD AND AD-PD PATIENTS

| | A9 | hippo | caudate | midbrain | medulla | putamen |
| --- | --- | --- | --- | --- | --- | --- |
| controls (n = 4–7) | 5.27 ± 2.84 | 3.89 ± 1.28 | 5.62 ± 0.72 | 1.87 ± 1.05 | 4.01 ± 1.42 | 4.56 ± 1.27 |
| AD patients (n = 11–13) | 6.90 ± 2.79 | 8.17 ± 2.83* | 6.09 ± 1.84 | 4.43 ± 1.87 | 6.32 ± 4.54 | 10.50 ± 2.11* |
| AD-PD patients (n = 4–7) | 4.49 ± 1.61 | 6.63 ± 0.57* | 8.95 ± 2.85 | 6.60 ± 2.22* | 8.11 ± 2.18 | 8.78 ± 3.01 |

*Statistically significantly differently from the DNA fragmentation values in the corresponding age-matched controls by ANOVA and Newman-Keul's test ($p < 0.05$).

Example 8

Apoptosis in MPTP Treated Mice

For all microscopy experiments, 7 month old C57BL/6 mice were injected twice with 25 mg/kg 1-methyl-4-phenyl-1,2,3,6-tetrahydropyridine (MPTP) intraperitoneally (i.p.) at an interval of 2 hours. After 48 hours the mice were perfused through the left ventricle with phosphate buffered saline (PBS) and then with 4% formaldehyde and 0.2% glutaraldehyde in PBS. The brains were coronally sliced into 50µ sections in a vibrating microtome.

All immunohistochemical studies were done 48 hours after injection of MPTP as significantly higher DNA fragmentation values (which may reflect the induction of apoptosis) were observed only after 48 hours following administration of MPTP.

To detect individual cells undergoing apoptosis, the In Situ Apoptosis Detection Kit (Oncor) was used. In this method, the fragmented DNA ends are extended with digoxigenin-dUTP. An anti-digoxigenin antibody then binds to the extension and is detected by a peroxidase reaction as previously described.

Tyrosine hydroxylase staining was done to identify dopaminergic neurons in the substantia nigra. The IgG polyclonal antibodies used were: a rabbit antibody to tyrosine hydroxylase; a sheep antibody to rabbit IgG and a rabbit antibody to horseradish peroxidase with the horseradish peroxidase coupled to the antibody[22]. The tyrosine hydroxylase-stained brain slices were mounted on glass slides, dehydrated and coverslipped with balsam.

Apoptotic cells with shrunken and fragmented nuclei were detected in dopaminergic neurons in the midbrain following MPTP administration. However, no apoptotic cells were observed when the mice were treated with 500 mg/kg nicotinamide 13 hours before administration of MPTP. Administration of 500 mg/kg nicotinamide alone for 13 hours did not generate any apoptotic cells.

It has been shown in previous studies that MPP+ can act as a substrate for xanthine oxidase producing MPP. and subsequently superoxide and hydroxyl radicals. Xanthine oxidase is located in brain endothelial cells and is probably activated during MPTP induced hypoperfusion. It was observed that addition of 0.1M nicotinamide is able to quench superoxide radicals produced by xanthine oxidase. 0.1M nicotinamide was also able to quench hydroxyl radicals generated by the addition of 0.4M hydrogen peroxide.

In the MPTP treated brains that were stained with a tyrosine hydroxylase antibody, condensed cells with fragmented nuclei can be clearly observed. In the nicotinamide prior to MPTP mice, the dopaminergic neurons were normal. No condensed cells with fragmented nuclei were observed.

A fluorimetric assay was also done to detect DNA fragmentation in the midbrain and in the striatum. C57BL/6 mice were divided into 5 groups with four animals in each group. Two groups of mice were treated twice with 25 mg/kg MPTP ip with two hours between injections. The brains were removed and sectioned 2 hours after the second injection for one group and 48 hours after the second injection for the other group. For a third group of mice, 500 mg/kg of nicotinamide (ip) was administered 13 hours prior to MPTP injection and the brains removed 48 hours after the second injection of MPTP. A fourth group of mice were treated with only 500 mg/kg nicotinamide. A fifth group was the control. Brains were removed and the midbrain and striatum isolated. A volume of 0.2 ml of ice cold lysing buffer (10 mM tris-HCl, pH 7.5, 1 mM EDTA, and 0.2 Triton X-100) was added to each section which was centrifuged at 12,000 g for 25 minutes to separate the intact from the fragmented DNA. The supernatant (containing the fragmented DNA) was transferred to a separate tube. 0.2 ml of the lysing buffer was added to the pellet with sonication for 10 seconds. The amount of DNA in the supernatant and pellet fractions was determined by a fluorimetric method, using the dye Hoechst 33258. DNA damage is normalized by dividing the amount of DNA in the supernatant by the total DNA in the pellet and supernatant and is expressed as the amount of damage per gram of tissue[17]. The levels of NAD were measured by an HPLC method[23].

TABLE 7

MPTP INDUCED DNA DAMAGE AND ITS PREVENTION BY NICOTINAMIDE

|  | MIDBRAIN | STRIATUM |
| --- | --- | --- |
| Control | 1.0937 ± 0.2191 | 1.0933 ± 0.3470 |
| Nicotinamide (−13 Hours) | 1.2462 ± 0.3292 | 1.2115 ± 0.1236 |
| MPTP (2 Hours) | 0.9108 ± 0.2233 | 0.9256 ± 0.0593 |
| MPTP (48 Hours) | 1.6373 ± 0.4567* | 1.2433 ± 0.2420 |
| Nicotinamide (−13 Hours) + MPTP (48 Hours) | 1.1311 ± 0.2999 | 1.2561 ± 0.1309 |

Results have been given as mean ± S.D. and can be expressed as the amount of DNA damaged per gram of tissue.
*Statistically significantly different from corresponding control values by ANOVA and Newman-Keul's test ($p < 0.05$).

Significant DNA fragmentation ($p<0.05$) was observed after 48 hours in the midbrain and not in the striatum after administration of 25 mg/kg MPTP twice (Table 7). Addition of nicotinamide was found to prevent the MPTP induced DNA fragmentation. The values of DNA fragmentation quantitated in this experiment is not absolute, but a comparison with the values for the corresponding controls.

It has been shown by previous studies that the midbrain is biochemically different from the striatum in terms of its response to MPTP toxicity[22]. Midbrain neuronal somas have nuclear DNA not present in striatal terminals. Of course, apoptosis of midbrain neurons causes loss of their striatal terminals. This makes the neurons more susceptible to oxidative stress induced DNA damage than their terminals. Though the DNA damage that is induced may be repaired over time by various enzymes, it is possible that transient DNA damage will affect protein synthesis or mRNA transcription. This may cause disruption in the normal processes in the brain.

Electron paramagnetic resonance (EPR) studies were done with 0.1 units/ml xanthine oxidase, 0.5 mM xanthine and 01.M DMPO in 0.1 glycine buffer (pH 8.3) containing 1 mM DETAPAC; 0.1M nicotinamide and 0.4M hydrogen peroxide. EPR spectra were measured at 23° and 100 kHz in a Bruker model ECS 106 spectrometer (Bruker, Karlsruhe, Germany). The EPR conditions were: modulation amplitude 0.483G, microwave power 20 mW and time constant 1.3 seconds.

Nicotinamide administration results in enhanced NAD levels. See Table 8. The enhanced NAD levels probably accelerates DNA repair mechanisms associated with PAD-PRP. Nicotinamide was administered in a dose of 500 mg/kg ip at times of either (b) 8 hours before sacrifice, (c) 13 before sacrifice and (d) twice at 9 and 4 hours before sacrifice. Mice were sacrificed and brains were removed and NAD levels were measured as before.

TABLE 8

THE ELEVATION OF NAD LEVELS (μmoles/g tissue) IN SIX BRAIN REGIONS WITH NICOTINAMIDE (NAM) (WITHOUT t-BuOOH)

| | cortex | striatum | thalamus | hippo | midbrain | cereb |
|---|---|---|---|---|---|---|
| control (a) | .30 ± .03 | .35 ± .04 | .33 ± .04 | .31 ± 03 | .28 ± .08 | .33 ± .09 |
| 8 hrs NAM (b) | .51 ± .01<br>a | .45 ± .02<br>a | .43 ± .03 | .38 ± .02 | .38 ± .04 | .44 ± .01 |
| 13 hrs NAM (c) | .42 ± .13 | .47 ± .07<br>a | .39 ± .07 | .38 ± 09 | .41 ± .08 | .42 ± .11 |
| 9 + 4 NAM (d) | .48 ± .04<br>a | .43 ± .04<br>a | .49 ± .06<br>a | .50 ± .04<br>a, b, c | .44 ± 03<br>a | .62 ± .01<br>a, b, c |

The letters a, b, c, indicate corresponding statistical significance by ANOVA with Newman-Keul's test. The groups indicated are control, intraperitoneal injection of nicotinamide (500 mg/kg) for 8 hours, 13 hours or 9 hours plus another injection for 4 hours (9 + 4) until sacrifice Administration of 500 mg/kg nicotinamide was seen to increase NAD levels from 0.28±0.08 μmol/g to 0.38±0.04 μmol/g in the midbrain and from 0.35±0.04 μmol/g to 0.45±0.04±μmol/g in the striatum. The levels of NAD remained high 13 hours after administration of nicotinamide. A large dose of nicotinamide was used as only a small fraction ultimately reaches the brain.

Nicotinamide is a weak inhibitor of poly(ADP-ribose) polymerase (PADPRP). In this example nicotinamide was injected 13 hours before administration of MPTP. Therefore, there is a possibility that all the nicotinamide may have not been present to inhibit PADPRP and may have been converted to NAD at the time the concentration of MPTP is high in the brain. This elevation in NAD levels may prevent DNA fragmentation and apoptosis.

We observe in our study that nicotinamide is able to prevent apoptosis as detected by tyrosine hydroxylase staining and the In Situ Apoptosis Detection Kit. It is also seen that nicotinamide is able to prevent DNA fragmentation in the midbrain as well as quench superoxide radicals formed by xanthine oxidase. Nicotinamide is also known to elevate NAD levels and ATP levels. Nicotinamide, therefore, appears to have two mechanisms of action: [1] it is able to quench radicals; and [2] it elevates NAD levels. Taken together, these findings suggest a novel role for nicotinamide in the prevention of apoptosis.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

What is claimed is:

1. A method for reducing the degree of neural apoptosis in a mammal due to a stroke which method comprises administering to the mammal an effective amount of a pharmaceutical composition consisting essentially of an NAD-related compound wherein the pharmaceutical composition administered reduces the degree of apoptosis.

2. The method of claim 1 wherein the NAD-related compound is selected from the group consisting of quinolinic acid; quinolinic acid ribonucleotide; nicotinamide; nicotinic acid; nicotinic acid ribonucleotide; nicotinic acid ribonucleotide, reduced form; nicotinamide ribonucleotide; nicotinamide ribonucleotide, reduced form; nicotinic acid adenine dinucleotide; nicotinic acid adenine dinucleotide, reduced form; nicotinamide adenine dinucleotide (NAD); nicotinamide adenine dinucleotide phosphate (NADP); nicotinamide adenine dinucleotide, reduced form (NADH); and nicotinamide adenine dinucleotide phosphate, reduced form (NADPH) and pharmaceutically acceptable salts thereof.

3. The method of claim 2 wherein the NAD-related compound is nicotinamide.

4. The method according to claim 1 wherein the NAD-related compound is administered up to 3 weeks after exposure of said mammal to the stroke.

5. The method according to claim 1 wherein the NAD-related compound is administered up to 14 hours before exposure of said mammal to the stroke.

6. A method for reducing the degree of neural apoptosis in a mammal due to exposure to a stroke which method comprises administering to the mammal a pharmaceutical composition consisting essentially of from about 1 to about 600 mg/kg of body weight of an NAD-related compound wherein the pharmaceutical composition administered reduces the degree of apoptosis.

7. The method of claim 6 wherein the NAD-related compound is selected from the group consisting of quinolinic acid; quinolinic acid ribonucleotide; nicotinamide; nicotinic acid; nicotinic acid ribonucleotide; nicotinic acid ribonucleotide, reduced form; nicotinamide ribonucleotide; nicotinamide ribonucleotide, reduced form; nicotinic acid adenine dinucleotide; nicotinic acid adenine dinucleotide, reduced form; nicotinamide adenine dinucleotide (NAD); nicotinamide adenine dinucleotide phosphate (NADP); nicotinamide adenine dinucleotide, reduced form (NADH); and nicotinamide adenine dinucleotide phosphate, reduced form (NADPH) and pharmaceutically acceptable salts thereof.

8. The method of claim 6 wherein the NAD-related compound is nicotinamide.

9. The method according to claim 6 wherein the NAD-related compound is administered up to 3 weeks after exposure of said mammal to the stroke.

10. The method according to claim 6 wherein the NAD-related compound is administered up to 14 hours before exposure of said mammal to the stroke.

* * * * *